(12) United States Patent
Galey et al.

(10) Patent No.: US 6,291,478 B1
(45) Date of Patent: Sep. 18, 2001

(54) COMPOUNDS OF THE BENZYLAMINODIACETAMIDE FAMILY, COMPOSITIONS COMPRISING THEM, PREPARATION PROCESS AND USES

(75) Inventors: Jean-Baptiste Galey, Aulnay-sous-Bois; Maria Dalko, Gif S/Yvette, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/524,570

(22) Filed: Mar. 13, 2000

(30) Foreign Application Priority Data

Mar. 11, 1999 (FR) .................................................. 99 03005

(51) Int. Cl.$^7$ .................................................. A01N 43/40
(52) U.S. Cl. .................. 514/316; 514/319; 514/331; 514/424; 514/534; 514/616; 514/785; 514/788; 546/187; 546/190; 546/205; 546/235; 548/500; 560/38; 560/41; 564/157
(58) Field of Search ..................... 546/187, 190, 546/205, 235; 548/500; 560/38, 41; 564/157; 514/316, 319, 331, 424, 534, 616, 785, 788

(56) References Cited

U.S. PATENT DOCUMENTS 5,658,581  8/1997  De Lacharriere et al. .......... 424/401
5,834,518  11/1998  Galey et al. .......... 514/566

FOREIGN PATENT DOCUMENTS 0 820 763   1/1998  (EP) .
0 864 563   9/1998  (EP) .
0 869 115  10/1998  (EP) .
2 728 793   7/1996  (FR) .
2 746 647  10/1997  (FR) .

OTHER PUBLICATIONS

T. Agner et al., "Quantification of the DMSO–Response—A Test for Assessment of Sensitive Skin", Clinical and Experimental Dermatology, vol. 14, No. 3, May 1989, pp. 214–217.
K. Lammintausta et al., "Mechanisms of Subjective (Sensory) Irritation", Dermatosen, vol. 36, No. 2, Mar./Apr. 1988, pp. 45–49.
English language Derwent Abstract of EP 0 864 563.
English language Derwent Abstract of FR 2 746 647.

*Primary Examiner*—Bernard Dentz
(74) *Attorney, Agent, or Firm*—Finnegan, Henderson, Farabow, Garrett & Dunner, L.L.P.

(57) ABSTRACT

The present application relates to novel compounds belonging to the benzylaminodiacetamide family which have good anti-irritant and soothing properties.

The invention also relates to their use in a composition comprising a physiologically acceptable medium, in particular in order to prevent and/or treat certain cutaneous disorders and more particularly in order to treat sensitive skins.

35 Claims, No Drawings

COMPOUNDS OF THE BENZYLAMINODIACETAMIDE FAMILY, COMPOSITIONS COMPRISING THEM, PREPARATION PROCESS AND USES

The present invention relates to novel benzylaminodiacetamide compounds and their derivatives, and to their use in, for example, cosmetics. The invention also relates to cosmetic compositions, including dermatological compositions, comprising these compounds.

In the field of cutaneous disorders, it is known that certain types of skin are more sensitive than others. However, the symptoms of sensitive skins were, until now, poorly characterized. As a result, these skin problems were poorly defined. No one knew the exact process implicated in the sensitivity of the skin. Some thought that a sensitive skin was a skin which reacted to cosmetic products. Others thought it was a matter of the skin reacting to a number of external factors not necessarily related to cosmetic products. Sensitive skins were also classified as allergic skins.

Tests have been developed in order to define sensitive skins. Such tests include, for example, those using lactic acid and DMSO, both of which are known to be irritant substances. See, for example, the article by K. Lammintausta et al., *Dermatoses*, Vol. 36, pages 45–49 (1988); and the article by T. Agner and J. Serup, *Clinical and Experimental Dermatology*, Vol. 14, pages 214–217 (1989).

Due to ignorance of the characteristics of sensitive skins, and until now, treatment was very difficult, if not impossible. In fact, sensitive skins were treated indirectly, for example by limiting the use, in cosmetic compositions, of products with an irritant nature, such as surfactants, preservatives or fragrances, as well as the use of certain cosmetic active principles.

It has been possible to determine the symptoms related to sensitive skins. These symptoms are generally subjective signs which are essentially dysaesthetic sensations. The term "dysaesthetic sensations" is understood to mean more or less painful sensations felt in a cutaneous region, such as smarting, pins and needles, itching or pruritus, burning sensations, warming sensations, discomfort, and stabbing pains. The symptoms related to the skin can also be microvascular manifestations of the cutaneous tissue, such as erythemas.

Moreover, a sensitive skin is not an allergic skin. In fact, an allergic skin is a skin which reacts to an external agent, namely an allergen, which triggers an allergic reaction. This relates to an immunological process which only takes place when an allergen is present, and which only affects sensitized subjects. By contrast, the essential characteristic of sensitive skin is, according to the present inventors, a mechanism of response to external factors which can affect any individual, even if individuals said to have sensitive skin react thereto faster than other individuals. This mechanism is not immunological; rather, it is non-specific.

Sensitive skins can be divided into two major clinical forms: irritable and/or reactive skins, and intolerant skins.

An irritable and/or reactive skin is a skin which reacts by a pruritus, that is to say by itching or by smarting in response to different factors such as the environment, emotions, food, wind, friction, shaving, soap, surfactants, hard water with a high calcium concentration, temperature variations, or wool. In general, these signs are associated with a dry skin, with or without sores, or with a skin which exhibits an erythema.

An intolerant skin is a skin which reacts with sensations of warming, stabbing pains, pins and needles, and/or redness to different factors such as the environment, the emotions, food, and certain cosmetic products. In general, these signs are also associated with a hyperseborrhoeic or acneic skin, with or without sores, and with an erythema.

"Sensitive" scalps have a less ambiguous clinical symptomatology: the sensations of pruritus and/or of smarting and/or of warming are essentially triggered by local factors such as friction, soap, surfactants, hard water with a high calcium concentration, shampoos, or lotions. These sensations are also sometimes triggered by factors such as the environment, the emotions, and/or food. An erythema and a hyperseborrhoea of the scalp and a dandruff state are frequently associated with the above signs.

Moreover, in certain anatomical regions, such as the major folds (inguinal, genital, axillary, popliteal, anal, submammary, or bend of the elbow regions) and the feet, sensitive skin is reflected by pruriginous sensations and/or dysaesthetic sensations (warming or smarting) related in particular to sweat, friction, wool, surfactants, certain cosmetic preparations, hard water with a high calcium concentration, and/or temperature variations.

A test has been developed in order to determine whether or not a skin is sensitive. In fact, after having carried out a great number of tests with the aim of defining a sensitive skin, it has surprisingly been found that there existed a connection between people with sensitive skin and those who reacted to a topical application of capsaicin.

The test with capsaicin comprises applying 0.05 ml of a cream comprising 0.075% of capsaicin to approximately 4 $cm^2$ of skin, and noting the appearance of subjective signs caused by this application, such as smarting, burning sensations, and itching. In subjects with sensitive skins, these signs appear between 3 and 20 minutes after application, and are followed by the appearance of an erythema which begins at the periphery of the application region.

The clinical signs of sensitive skin are essentially subjective: smarting, pins and needles, pruritus, stabbing pains, or warming sensations, and the signs are sometimes associated with erythemas. These signs are due to non-specific external factors. The symptoms appear essentially localized on the face, on the neck, and on the scalp, but can also appear anywhere on the body.

After much research, the inventors have discovered novel compounds belonging to the benzylaminodiacetamide family which have good anti-irritant and soothing properties. Suitably, these compounds can make it possible to avoid cutaneous irritation, dysaesthetic sensations, pruritus of the skin, mucous membranes, and erythema, sores, and/or warming sensations, in a composition suitable for topical use, such as a composition suitable for treating sensitive skins.

One object of the present invention is to provide a composition comprising, in a physiologically acceptable medium, at least one compound corresponding to the formula (I) described herein below.

The invention also relates to compounds corresponding to the formula (Ia) described herein below.

Another object of the invention is a process for the preparation of a compound of formula (I) in which a diacid is reacted with a dehydrating agent, so as to obtain an intermediate anhydride which makes coupling with a first amine or a first alcohol possible, and then, in a second stage, a coupling agent is added which makes coupling of the said diacid with a second amine or a second alcohol possible.

Yet another object if the present invention is the use of at least one compound of formula (I) in a composition comprising a product with an irritant effect, in order to weaken, indeed even eliminate, the irritant effect.

Another object of the invention is the use of at least one compound of formula (I) in a cosmetic composition, or for the preparation of a physiologically acceptable composition, in order to prevent and/or treat cutaneous disorders, including but not limited to cutaneous irritations, sores, redness, dysaesthetic sensations, warming sensations, and/or pruritus of the skin and/or mucous membranes.

Another object of the invention is a cosmetic treatment process, characterized in that a cosmetic composition as defined above is applied to the skin, to the hair, and/or to the mucous membranes.

Furthermore, it has been found that, advantageously, the compounds of formula (I) can be used in combination with commonly used products having an irritant effect. Such commonly used products include those in the cosmetics field, including certain cosmetic active principles. The presence of at least one compound of formula (I) in a composition comprising such a product having an irritant effect makes it possible to greatly weaken, indeed even to eliminate, this irritant effect. In addition, this makes it possible, for the purpose of improved effectiveness, to increase the amount of the said product having an irritant effect relative to the amount normally used.

In the composition according to the invention, the compounds correspond to the following formula (I):

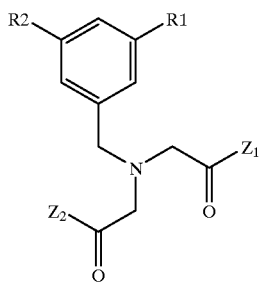

in which:

$R_1$ and $R_2$, which are identical or different, are chosen from hydrogen, $CH_3$, $CF_3$, $OCH_3$, and OH radicals, $Z_1$ is chosen from $NX_1X_2$ and $OX_1$ radicals, and $Z_2$ is chosen from $NX_3X_4$ and $OX_3$ radicals, in which:

$X_1$ and $X_3$, which are identical or different, represent:
  a $C_1$–$C_2$ alkyl radical, wherein the $C_1$–$C_{12}$ alkyl radical is unsubstituted, or substituted by:
    at least one group chosen from OH, $NH_2$, SH, CN, $CF_3$, halogen, COOH, CONHR', COOR', OR', and SR', with R' representing a $C_1$–$C_4$ alkyl, or
    at least one homocyclic or heterocyclic $C_3$–$C_7$ aliphatic or aromatic ring; or
  an aryl radical which is unsubstituted or substituted by
    at least one group chosen from OH, $NH_2$, SH, CN, $CF_3$, halogen, COOH, CONHR', COOR', OR', and SR' groups with R' representing a $C_1$–$C_4$ alkyl, or
    at least one homocyclic or heterocyclic $C_3$–$C_7$ aliphatic or aromatic ring; and $X_2$ is a hydrogen atom or, together with N and $X_1$, forms a 5- or 6-membered ring; and, independently, $X_4$ is a hydrogen atom or, together with N and $X_3$, forms a 5- or 6-membered ring;

Thus, the following represents non-limiting examples of available combinations when $Z_1$ is $NX_1X_2$ and/or $Z_2$ is $NX_3X_4$:

$X_2$ is H and $X_4$ is H;

$X_2$ is H and $X_4$, together with $X_3$ and nitrogen, forms a ring;

$X_4$ is H and $X_1$, together with $X_2$ and nitrogen, forms a ring; and $X_2$, together with $X_1$, and nitrogen, forms a ring; and $X_4$, together with $X_2$ and nitrogen, forms a ring.

The rings formed by $NX_1X_2$ or $NX_3X_4$ may be hydrocarbon rings which are saturated or unsaturated and which are interrupted only by the nitrogen atom.

In certain embodiments, the $R_1$ and $R_2$ radicals may each represent $CF_3$, the $Z_1$ and $Z_2$ radicals may represent piperidine or methionamide, and the $R_1$ and $R_2$ radicals may be identical.

Furthermore, when at least one of the $R_1$ or $R_2$ radicals is other than a hydrogen atom, the compounds of formula (I) are novel compounds.

Thus, another object of the invention is compounds corresponding to the following formula (Ia):

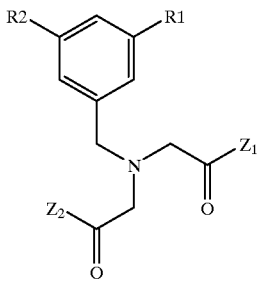

in which:

$R_1$ and $R_2$, which are identical or different, are chosen from hydrogen or $CH_3$, $CF_3$, $OCH_3$ and OH radicals, with the proviso that at least one of the $R_1$ and $R_2$ radicals is other than hydrogen; and $Z_1$ and $Z_2$ have the same meaning as in the above formula (I).

The compounds of formulae (I) and (Ia) can be prepared according to the following general synthetic scheme:

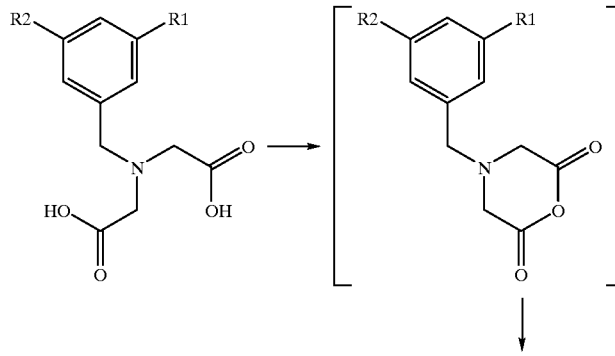

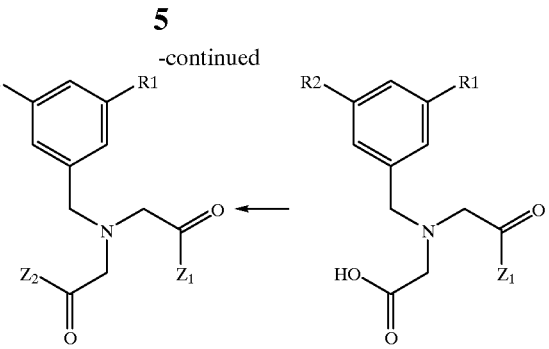

Generally, the process for the preparation of the compounds of formulae (I) and (Ia) comprises a conventional coupling between a diacid and two amines or alcohols.

For example, in a first stage, the said diacid can be reacted with a dehydrating agent so as to obtain an intermediate anhydride which makes possible coupling with the first amine or the first alcohol, and then, in a second stage, a coupling agent can be added which makes possible coupling of the said diacid with the second amine or the second alcohol.

A process which makes possible the preparation of the compounds of formulae (I) and (Ia) is given hereinbelow, by way of indication but without implied limitation.

In a first stage, the diacid can be prepared according to the following scheme:

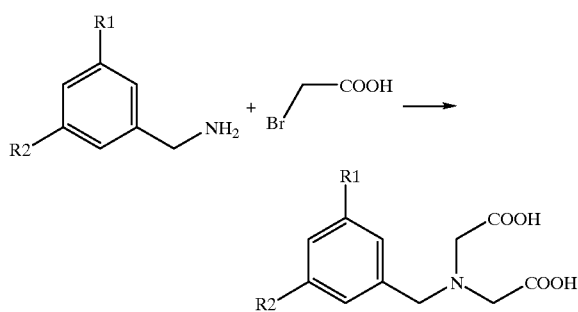

Benzylamine, optionally disubstituted in the 3- and/or 5-position, is dissolved in a protic solvent, such as ethanol. An excess of at least 2 equivalents of sodium bromoacetate is added. The pH of the medium is adjusted to 10 by addition of a strong base. The mixture is stirred at a temperature ranging from 30 to 60° C., for example 35–45° C., for a period of time ranging from 2 to 12 hours, for example 5–7 hours, while maintaining the pH between 9 and 11.

The medium is then cooled and washed with an organic solvent. The remaining aqueous solution is reacidified. The diacid is obtained in the form of a precipitate, which is filtered off and dried.

In a second stage, the diamide can be prepared according to the following scheme:

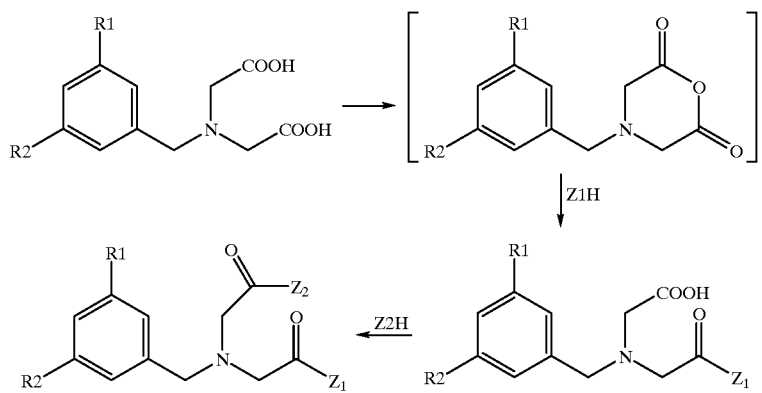

The diacid is dissolved in an anhydrous dipolar aprotic solvent, such as DMF (dimethylformamide), in the presence of a dehydrating agent, for example EDCI (N-(3-dimethylaminopropyl)-N'-ethylcarbodiimide hydrochloride), so as to generate the anhydride in situ. The medium is stirred for 1 to 6 hours at a temperature ranging from 20 to 40° C. under an inert atmosphere.

One equivalent of the first amine or alcohol $Z_1H$ is then added. The mixture is stirred under an inert atmosphere for 10 to 30 hours at a temperature ranging from 20 to 40° C.

One equivalent of the second amine or alcohol $Z_2H$ is then added in the presence of a catalytic amount of a non-nucleophilic amine, such as triethylamine or diisopropylethylamine, and in the presence of one equivalent of a coupling agent, such as PyBOP ((benzotriazol-1-yloxy)tripyrrolidinophosphonium hexafluorophosphate).

The mixture is subsequently stirred under an inert atmosphere ranging from 20 to 40° C. for approximately 10 to 30 hours. The reaction medium is then acidified and the aqueous phase is extracted three times with an organic solvent.

The various organic phases are collected and then washed successively with acidic, basic, and then neutral aqueous solutions. After drying, filtering, and evaporating, the diamide formed is purified by chromatography or crystallization.

Mention may be made, among the amines capable of being employed, of the compounds with the following formulae and their derivatives:

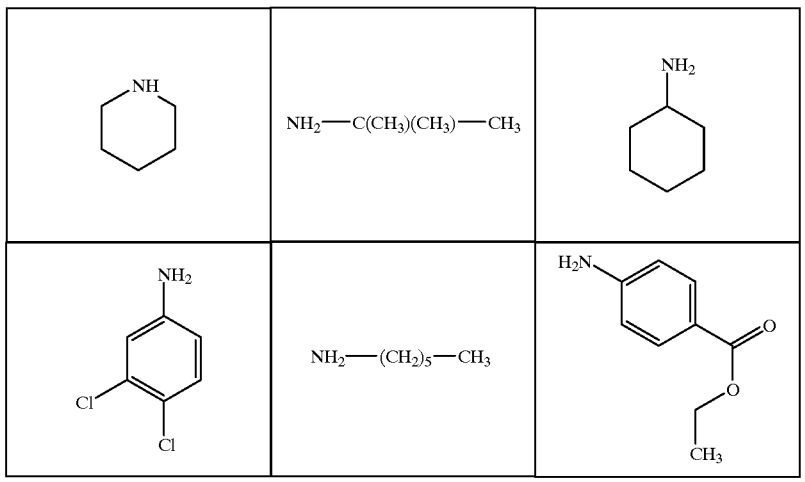

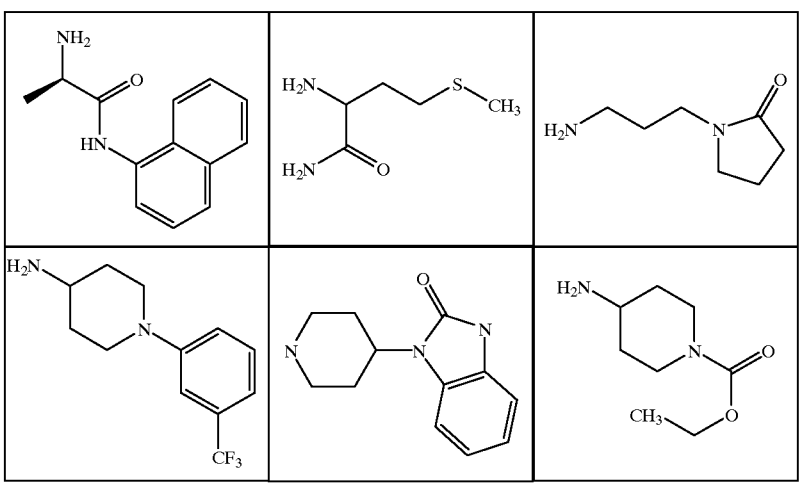

Mention may be made, among suitable compounds of formula (I) according to the invention, of:

2-[(3,5-bis(trifluoromethyl)benzyl)(hexylcarbamoylmethyl)amino]-N-(3,4-dichlorophenyl)acetamide;

2-{2-[(3,5-bis(trifluoromethyl)benzyl)(2-oxo-2-(piperidin-1-yl)ethyl)amino]acetylamino}-4-(methylsulphanyl)butyramide; and 2-[(3,5-bis(trifluoromethyl)benzyl)(hexylcarbamoylmethyl)amino]-N-(tert-butyl)acetamide.

The compounds of formula (I) can be employed alone or as a mixture in a composition which comprises a physiologically acceptable medium, such as a cosmetic composition, which furthermore comprises a cosmetically acceptable medium.

The compound(s) of formula (I) and the compositions comprising them can be used to prevent and/or treat cutaneous disorders, such as cutaneous irritations, sores, redness, dysaesthetic sensations, warming sensations, and/or pruritus of the skin and/or mucous membranes. They can be used to treat sensitive skins.

The amount of compound of formula (I) present in the composition according to the invention is, of course, a function of the desired effect. Thus, the composition can comprise at least one compound of formula (I) in an amount ranging from 0.001% to 20% of the total weight of the composition. In one embodiment, the amount may range from 0.01% to 10% by weight. In another embodiment, the amount may range from 0.1% to 5% by weight of the total weight of the composition.

The physiologically acceptable medium in which the compounds according to the invention can be employed, as well as its constituents, their amount, the pharmaceutical dosage form of the composition, and its method of preparation can be chosen by a person of ordinary skill in the art on the basis of his or her overall knowledge, according to the type of composition desired.

For application to the skin, the composition can be in the form of, for example, an aqueous or oily solution; a dispersion of the lotion or serum type; emulsions with a liquid or semi-liquid consistency of the milk type, obtained by dispersion of a fatty phase in an aqueous phase (oil-in-water) or vice versa (water-in-oil); suspensions or emulsions with a soft consistency of the aqueous or anhydrous gel or cream type; microcapsules or microparticles; or vesicular dispersions of the ionic and/or nonionic type.

For application to the hair, the composition can be in the form of aqueous, alcoholic, or aqueous/alcoholic solutions; in the form of creams, gels, emulsions, or foams; or in the form of aerosol compositions which also comprise a pressurized propellant.

Generally, this medium can be anhydrous or aqueous. It can thus comprise an aqueous phase and/or a fatty phase.

When the composition is an emulsion, the proportion of the fatty phase can range from 5% to 80% by weight and, in another embodiment, from 5% to 50% by weight relative to the total weight of the composition. The oils, the waxes, the emulsifiers, and the coemulsifiers used in the composition in the emulsion form are chosen from those conventionally used in the field under consideration. The emulsifier and the coemulsifier can be present in the composition in an amount ranging from 0.3% to 30% by weight relative to the total weight of the composition. In a certain embodiment, the amount can range from 0.5% to 20% by weight. The emulsion can, in addition, comprise lipid vesicles.

When the composition is an oily gel or solution, the fatty phase can represent more than 90% of the total weight of the composition.

Mention may be made, as oils or waxes which can be used in the invention, of mineral oils (such as liquid petrolatum), vegetable oils (such as the liquid fraction of karite butter, and sunflower oil), animal oils (such as perhydrosqualene), synthetic oils (such as purcellin oil), silicone oils or waxes (such as cyclomethicone) and fluorinated oils (such perfluoropolyethers), beeswax, carnauba wax, or paraffin wax. Fatty alcohols and fatty acids (stearic acid, for example) can be added to these oils.

Mention may be made, as emulsifiers which can be used in the invention, of, for example, glyceryl stearate, polysorbate 60, and the PEG-6/PEG-32/glycol stearate mixture sold under the name of TEFOSE® 63 by Gattefosse.

The composition according to the invention can comprise adjuvants which are typically used in the art, such as hydrophilic or lipophilic gelling agents, hydrophilic or lipophilic additives, active principles, for example cosmetic active principles, preservatives, antioxidants, solvents, fragrances, fillers, pigments, screening agents, odor absorbers, and dyes. These adjuvants, depending on their nature, can be introduced in the fatty phase, in the aqueous phase, and/or in lipid spherules.

Mention may be made, as solvents which can be used according to the invention, of $C_1$–$C_6$ alcohols such as, for example, ethanol, isopropanol, and propylene glycol.

Mention may be made, as hydrophilic gelling agents which can be used according to the invention, of carboxyvinyl polymers (such as carbomer), acrylic copolymers (such as acrylate/alkyl acrylate copolymers), polyacrylamides, polysaccharides (such as hydroxypropylcellulose), natural gums, and clays.

Mention may be made, as lipophilic gelling agents, of modified clays (such as bentones), metal salts of fatty acids (such as aluminium stearates), hydrophobic silica, ethylcellulose, or polyethylene.

The composition can comprise hydrophilic active principles such as proteins or protein hydrolysates, amino acids, polyols, urea, allantoin, sugars and sugar derivatives, water-soluble vitamins, plant extracts, and hydroxy acids. Use may be made, among lipophilic active principles, of retinol (vitamin A) and its derivatives, tocopherol (vitamin E) and its derivatives, essential fatty acids, ceramides, essential oils, and salicylic acid and its derivatives.

In the context of the invention, the composition can comprise, in combination with the compound or compounds of formula (I), known active agents which may be used for the prevention and/or the treatment of cutaneous conditions. Mention may be made among these active agents, by way of example, of:

agents which modulate cutaneous pigmentation and/or proliferation and/or differentiation, such as retinoic acid and its isomers, retinol and its esters, vitamin D and its derivatives, estrogens such as oestradiol, kojic acid, and hydroquinone;

antibacterials, such as clindamycin phosphate, erythromycin, and antibiotics from the tetracycline class;

agents for combating parasites, such as metronidazole, crotamiton, and pyrethroids;

antifungals, such as compounds belonging to the imidazole class, including econazole, ketoconazole, and miconazole or a salt thereof, and polyene compounds, such as amphotericin B, compounds of the allylamine family, such as terbinafine, and octopirox;

antiviral agents, such as acyclovir;

steroidal anti-inflammatory agents, such as hydrocortisone, betamethasone valerate, and clobetasol propionate;

non-steroidal anti-inflammatory agents, such as ibuprofen and its salts, diclofenac and its salts, acetylsalicylic acid, acetaminophen, and glycyrrhetinic acid;

anaesthetic agents, such as lidocaine hydrochloride and its derivatives;

antipruriginous agents, such as thenaldine, trimeprazine and cyproheptadine;

keratolytic agents, such as α- and β-hydroxycarboxylic acids and β-ketocarboxylic acids, their salts, amides or esters, and hydroxy acids, such as glycolic acid, lactic acid, salicylic acid, citric acid and generally fruit acids, and 5-(n-octanoyl) salicylic acid;

agents for combating free radicals, such as α-tocopherol and its esters, superoxide dismutases, certain metal chelating agents, and ascorbic acid and its esters;

antiseborrhoeics, such as progesterone;

antidandruff agents, such as octopirox and zinc pyrithione; and antiacne agents, such as retinoic acid and benzoyl peroxide.

Furthermore, as mentioned above, the compounds of formula (I) can be used in combination with products having an irritant effect, such as active principles commonly used in the cosmetics field. This is because the presence of the compounds of formula (I) can make it possible to greatly weaken, indeed even to eliminate, this irritant effect. In addition, this makes it possible, for the purpose of improved effectiveness, to increase the amount of product with an irritant effect relative to the amount of product normally used.

Mention may be made, as products with an irritant effect, of, for example, surfactants (including ionic or non-ionic), preservatives, organic solvents, or active principles such as α-hydroxy acids (including, for example, citric, malic, glycolic, tartaric, mandelic, or lactic acid), β-hydroxy acids (including salicylic acid and its derivatives), α-keto acids, β-keto acids, retinoids (such as retinol, retinal, and retinoic acid), anthralins (such as dioxyanthranol), anthranoids, peroxides (such as benzoyl peroxide), minoxidil, lithium salts, antimetabolites, vitamin D and its derivatives, hair dyes or colorants (such as para-phenylenediamine and its derivatives, and aminophenols), perfuming alcoholic solutions (such as fragrances, eaux de toilette, aftershaves, and deodorants), antiperspirant agents (including certain aluminum salts), depilatory or permanent-wave active principles (such as thiols) or depigmenting active principles (such as hydroquinone).

In another embodiment of the invention, the composition according to the invention can additionally comprise at least one compound which decreases the synthesis, the release, and/or the activity of at least one mediator of inflammation. Mention may be made, among these compounds, of those listed in French Patent Application FR 2,746,647, the contents of which is specifically incorporated herein by reference in its entirety. Mention may also be made of substance P and/or CGRP antagonists, NO-synthase inhibitors, bradykinin antagonists, cytokine antagonists, histamine antagonists, and/or α-type tumor necrosis factor (TNF-α) antagonists. These compounds can be present in an amount ranging from 0.001% to 10% by weight, relative to the total weight of the composition. In a certain embodiment, the amount can range from 0.01% to 2% by weight, relative to the total weight of the composition.

The compositions according to the invention can be provided in the form of cleansing, protective, treatment, or care creams for the face, hands, feet, large anatomical folds, or for the body (for example, day creams, night creams, make-up removal creams, foundation creams, or antisun creams); of liquid foundations, make-up removal milks, protective or care body milks, or antisun milks; of lotions, gels, or foams for caring for the skin, such as cleansing lotions, antisun lotions, or artificial tanning lotions; bath compositions or deodorant compositions comprising a bactericidal agent; aftershave gels or lotions; depilatory creams; compositions for combating insect stings; pain-control compositions; or compositions for treating certain cutaneous disorders, such as eczema, rosacea, psoriasis, lichens, or severe pruritus.

The compositions according to the invention can also be provided in the form of solid compositions which make up cleansing bars or soaps.

The compositions can also be packaged in the form of an aerosol composition further comprising a pressurized propellant.

The compositions can also be in a form for hair care, such as, for example, a shampoo, a hair-setting lotion, a treating lotion, a styling cream or gel, a dye composition (such as oxidation dyes), optionally in the form of coloring shampoos, hair-restructuring lotions, a permanent-wave composition (such as a composition for the first step of a permanent wave), a lotion or gel for combating hair loss, a shampoo for combating parasites, and the like.

The compositions can also be in a form suitable for oral use, for example a toothpaste. In this case, the composition can comprise adjuvants and additives typically used for compositions for buccal use, such as surface-active agents, thickening agents, humectant agents, polishing agents such as silica, various active ingredients such as fluorides, including sodium fluoride, and optionally sweetening agents, such as sodium saccharinate.

An additional object of the present invention is a cosmetic treatment process, characterized in that a cosmetic composition as described above comprising at least one compound of formula (I) in a cosmetically acceptable medium is applied to the skin, the hair, and/or the mucous membranes.

The cosmetic treatment process of the invention can be employed, by way of example, by applying the cosmetic compositions as defined above according to the usual technique for the use of these compositions. For example: application of make-up removal creams, gels, serums, lotions or milks, or of antisun compositions to the skin, or to dry hair, application of a hair lotion to wet hair or of shampoos, or application of a dentifrice to the gums.

The invention is illustrated in more detail in the following non-limiting examples.

EXAMPLE 1

Preparation of 2-[(3,5-bis(trifluoromethyl)-benzyl)(hexylcarbamoylmethyl)aminol]-N-(3,4-dichlorophenyl)acetamide 1st stage: synthesis of 3,5-bis(trifluoromethyl)benzylamine-N,N-diacetic acid

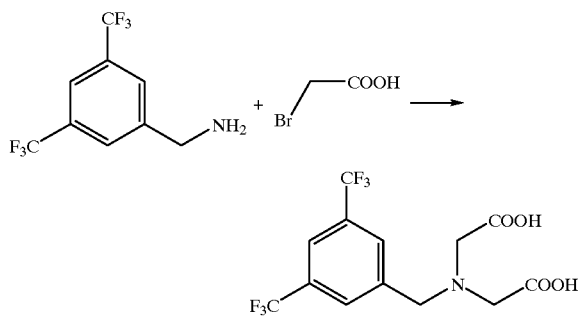

15 g (50 mmol) of 3,5-bis(trifluoromethyl)benzylamine were dissolved in 40 ml of ethanol. A mixture of 13.7 g (100 mmol) of bromoacetic acid and 8.3 g (100 mmol) of $NaHCO_3$, in solution in 10 ml of water, was added dropwise. The pH of the medium was adjusted to 10 by addition of sodium hydroxide solution. The mixture was stirred at 40° C. for 6 hours while maintaining the pH at 10 by addition of sodium hydroxide.

The medium was then cooled and washed three times with 50 ml of $CH_2Cl_2$. The remaining aqueous solution was reacidified with HCl to a pH of the order of 1–2.

The precipitated product was filtered off. The solid obtained was dried under vacuum at 50° C. in the presence of $P_2O_5$.

18 g of product were obtained, which product was in the form of a white powder (yield of 100%).

Its characterization by $^1$H NMR (200 MHz, $d_6$-DMSO) gave the following result:

δ ppm: 3.5 (4H, s, $2H_1$, $2H_2$), 4.1 (2H, s, $2H_3$), 8.0 (1H, s, $H_7$), 8.2 (2H, s, $H_5$, $H_9$), 12.5 (2H, broad s, COO$\underline{H}$).

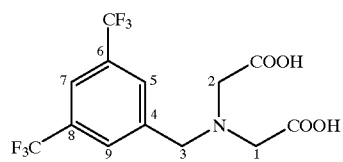

2nd stage: synthesis of 2-[(3,5-bis(trifluoromethyl)-benzyl)(hexylcarbamoylmethyl)amino]-N-(3,4-dichlorophenyl)acetamide

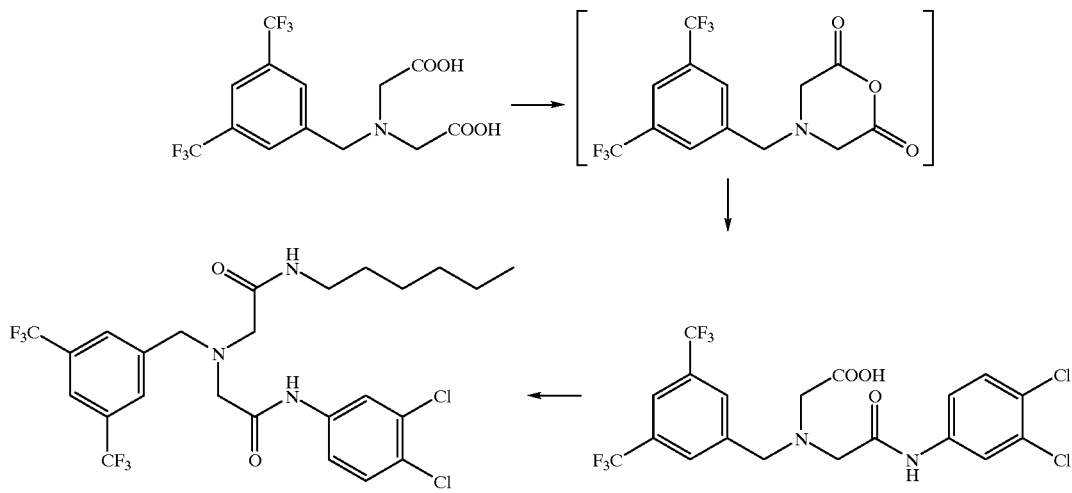

300 mg of diacid prepared in stage 1 was dissolved in 15 ml of anhydrous DMF. 168 mg (1.05 equivalents) of EDCl (N-(3-dimethylaminopropyl)-N'-ethylcarbodiimide hydrochloride) was added, and stirring was maintained for 4 hours at room temperature under an inert atmosphere (argon).

135 mg (1 eq.) of 3,4-dichloroaniline, in solution in 5 ml of DMF, was added and the mixture was stirred at room temperature under argon for 20 hours.

The following were subsequently added at room temperature:

- 84 mg (1 eq.) of hexylamine, in solution in 5 ml of DMF,
- 300 ml (0.2 eq.) of diisopropylethylamine, and
- 435 mg of PyBOP (1 eq.) ((benzotriazol-1-yloxy) tripyrrolidinophosphonium hexafluorophosphate), in solution in 5 ml of anhydrous DMF.

The mixture was subsequently stirred at room temperature under argon for 20 hours.

The reaction mixture was acidified by addition of 10% HCl and the aqueous phase was extracted three times with 20 ml of ethyl acetate. The various organic phases were collected and then washed successively with 10% HCl, saturated $NaHCO_3$ and finally saturated NaCl solutions. After drying over $Na_2SO_4$, filtering and evaporating, 450 mg of a yellow oil were recovered. This oil was purified by flash chromatography on silica gel ($CH_2Cl_2$/MeOH=1%).

After purification, 304 mg of product were obtained, i.e., 62% yield, the product having the appearance of a yellow solid.

Its characterization by $^1$H NMR (200 MHz) in $CDCl_3$ gave a spectrum in accordance with the structure of the expected product.

δ ppm: 0.78 (3H, t, $3H_{12}$), 1.1 (6H, m, $2H_{11}$, $2H_{10}$, $2H_9$), 1.4 (2H, m, $2H_8$), 3.15 (2H, q, $2H_7$), 3.3 (2H, s, $2H_4$), 3.35 (2H, s, $2H_3$), 3.9 (2H, s, $2H_{19}$), 5.8 (1H, t, H6), 7.3 (1H, s, $H_{aryl}$), 7.37 (1H, d, $H_{aryl}$), 7.73 (1H, s, $H_{aryl}$), 7.77 (2H, s, $H_{aryl}$), 7.88 (1H, d, $H_{aryl}$)

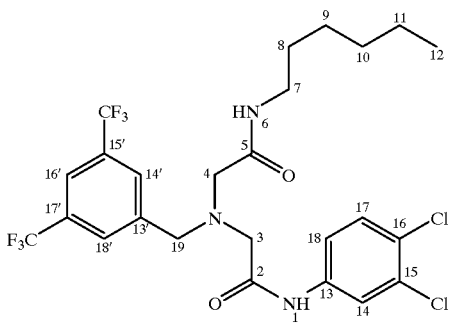

EXAMPLE 2

Two other compounds were prepared, according to the same process as in Example 1, from the starting compounds given hereinbelow.

The structures of the compounds obtained were confirmed by coupled HPLC/mass spectrometry using the electrospray ionization technique at atmospheric pressure.

The masses observed by ESI/MS for these two compounds are shown hereinbelow.

1) Starting Compounds 3,5-bis(trifluoromethyl)benzylamine
compound of formula:

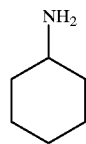

compound of formula:

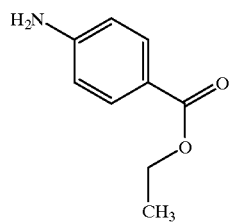

The compound of formula:

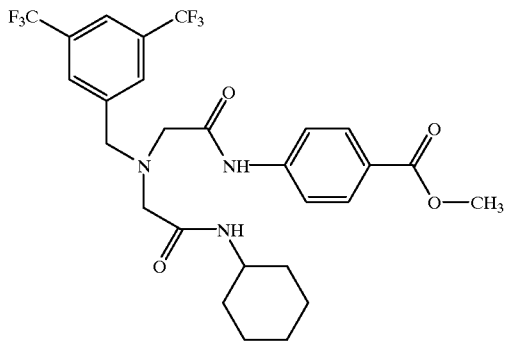

was then obtained.

Its observed mass was, by MS (ES+/−): 574.4 g (M+Na)

2) Starting Compounds 3,5-bis(trifluoromethyl)benzylamine
compound of formula:

compound of formula: $NH_2$—$C(CH_3)(CH_3)$—$CH_3$

The final compound of formula:

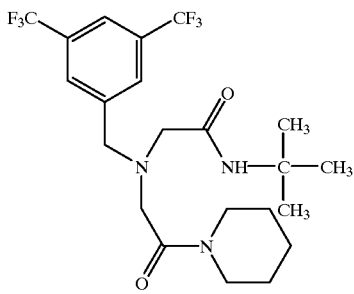

was then obtained.

Its observed mass was, by MS (ES+/−): 504.4 g (M+Na)

EXAMPLE 3

The compounds corresponding to the following formulae were also prepared according to the same process:

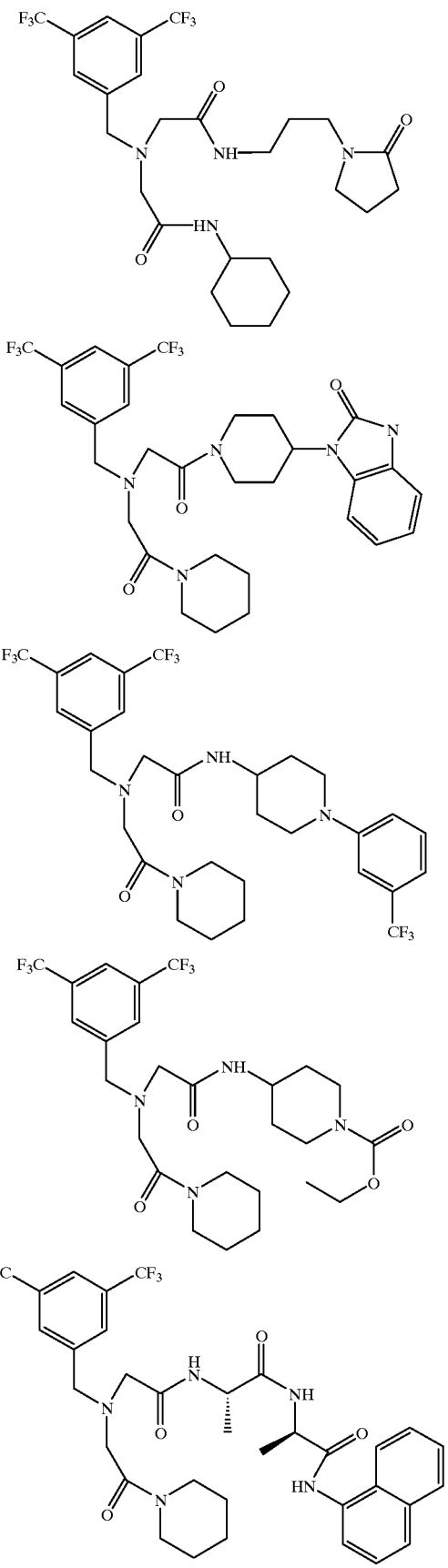

-continued

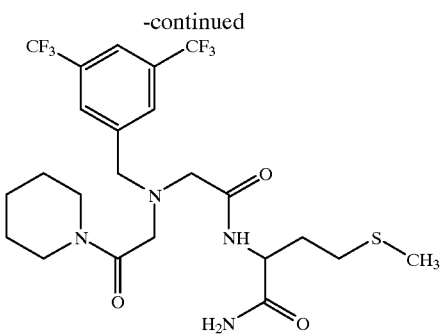

EXAMPLE 4

A care cream for the face (oil-in-water emulsion) was prepared comprising:

| | |
|---|---|
| Compound of Example 1 | 1.00 |
| Glyceryl stearate | 2.00 |
| Polysorbate 60 (TWEEN 60, sold by ICI) | 1.00 |
| Stearic acid | 1.40 |
| Triethanolamine | 0.70 |
| Carbomer | 0.40 |
| Liquid fraction of karite butter | 12.00 |
| Perhydrosqualene | 12.00 |
| Antioxidant | q.s. |
| Fragrance | q.s. |
| Preservative | q.s. |
| Water | q.s. for 100% |

EXAMPLE 5

A shampoo was prepared comprising:

| | |
|---|---|
| Compound of Example 1 | 0.50 |
| Hydroxypropylcellulose (KLUCEL H from Hercules) | 1.00 |
| Fragrance | q.s. |
| Preservative | q.s. |
| Water | q.s. for 100% |

EXAMPLE 6

A pain-relieving gel was prepared comprising:

| | |
|---|---|
| Compound of Example 1 | 1.00 |
| Hydroxypropylcellulose (KLUCEL H from Hercules) | 1.00 |
| Antioxidant | 0.05 |
| Lidocaine hydrochloride | 2.00 |
| Isopropanol | 40.00 |
| Preservative | q.s. |
| Water | q.s. for 100% |

EXAMPLE 7

An after-sun care cream (oil-in-water emulsion) was prepared comprising:

| | |
|---|---|
| Compound of Example 1 | 0.80 |
| Glyceryl stearate | 2.00 |
| Polysorbate 60 (TWEEN 60, sold by the company ICI) | 1.00 |
| Stearic acid | 1.40 |
| Glycyrrhetinic acid | 2.00 |
| Triethanolamine | 0.70 |
| Carbomer | 0.40 |
| Liquid fraction of karite butter | 12.00 |
| Sunflower oil | 10.00 |
| Antioxidant | q.s. |
| Fragrance | q.s. |
| Preservative | q.s. |
| Water | q.s. for 100% |

EXAMPLE 8

A care gel for the face was prepared comprising:

| | |
|---|---|
| Compound of Example 1 | 0.50 |
| Vichy thermal water | 10.00 |
| Hydroxypropylcellulose (KLUCEL H, sold by Hercules) | 1.00 |
| Antioxidant | q.s. |
| Isopropanol | 40.00 |
| Preservative | q.s. |
| Water | q.s. for 100% |

EXAMPLE 9

An after-sun care cream (oil-in-water emulsion) was prepared comprising:

| | |
|---|---|
| Compound of Example 1 | 5.00 |
| Vichy thermal water | 10.00 |
| Glyceryl stearate | 2.00 |
| Polysorbate 60 (TWEEN 60, sold by ICI) | 1.00 |
| Stearic acid | 1.40 |
| Glycyrrhetinic acid | 2.00 |
| Triethanolamine | 0.70 |
| Carbomer | 0.40 |
| Liquid fraction of karite butter | 12.00 |
| Sunflower oil | 10.00 |
| Antioxidant | q.s. |
| Fragrance | q.s. |
| Preservative | q.s. |
| Water | q.s. for 100% |

EXAMPLE 10

A pain-relieving gel was prepared comprising:

| | |
|---|---|
| Compound of Example 1 | 5.00 |
| SPANTIDE II | 0.05 |
| Hydroxypropylcellulose (KLUCEL H, sold by Hercules) | 1.00 |
| Antioxidant | q.s. |
| Lidocaine hydrochloride | 2.00 |
| Isopropanol | 40.00 |
| Preservative | q.s. |
| Water | q.s. for 100% |

The present invention may be embodied in other specific forms without departing from its spirit or essential characteristics. The described embodiments are to be considered in all respects as illustrative only and not restrictive. The scope of the invention is, therefore, indicated by the appended claims, rather than by the foregoing description. All changes which come within the meaning and range of equivalency of the claims are to be embraced within their scope.

What is claimed is:

1. A compound corresponding to the following formula (Ia):

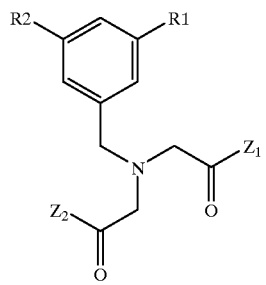

in which:

R$_1$ and R$_2$, which are identical or different, are chosen from hydrogen, a CH$_3$ radical, a CF$_3$ radical, a OCH$_3$ radical, and a OH radical;

Z$_1$ is chosen from an NX$_1$X$_2$ radical and an OX$_1$ radical, and Z$_2$ is chosen from a NX$_3$X$_4$ radical and an OX$_3$ radical, in which:

X$_1$ and X$_3$, which are identical or different, represent:
a C$_1$–C$_{12}$ alkyl radical, wherein the C$_1$–C$_{12}$ alkyl radical is unsubstituted, or substituted by:
at least one group chosen from OH, NH$_2$, SH, CN, CF$_3$, halogen, COOH, CONHR', COOR', OR', and SR', with R' representing a C$_1$–C$_4$ alkyl, or
at least one homocyclic or heterocyclic C$_3$–C$_7$ aliphatic or aromatic ring; or
an aryl radical which is unsubstituted or substituted by
at least one group chosen from OH, NH$_2$, SH, CN, CF$_3$, halogen, COOH, CONHR', COOR', OR', and SR' groups with R' representing a C$_1$–C$_4$ alkyl, or
at least one homocyclic or heterocyclic C$_3$–C$_7$ aliphatic or aromatic ring; and X$_2$ is a hydrogen atom or, together with N and X$_1$, forms a 5- or 6-membered ring; and, independently,
X$_4$ is a hydrogen atom or, together with N and X$_3$, forms a 5- or 6-membered ring;

with the proviso that at least one of the R$_1$ and R$_2$ radicals is other than hydrogen.

2. A compound according to claim 1, wherein each of the R$_1$ and R$_2$ radicals is CF$_3$.

3. A compound according to claim 1, wherein the Z$_1$ and Z$_2$ radicals, which are the same or different, are chosen from piperidine and methionamide.

4. A compound according to claim 1, wherein:
each of the R$_1$ and R$_2$ radicals is CF$_3$, and
the Z$_1$ and Z$_2$ radicals, which are the same or different, are chosen from piperidine and methionamide.

5. A compound according to claim 1, chosen from at least one compound corresponding to one of the following formulae:

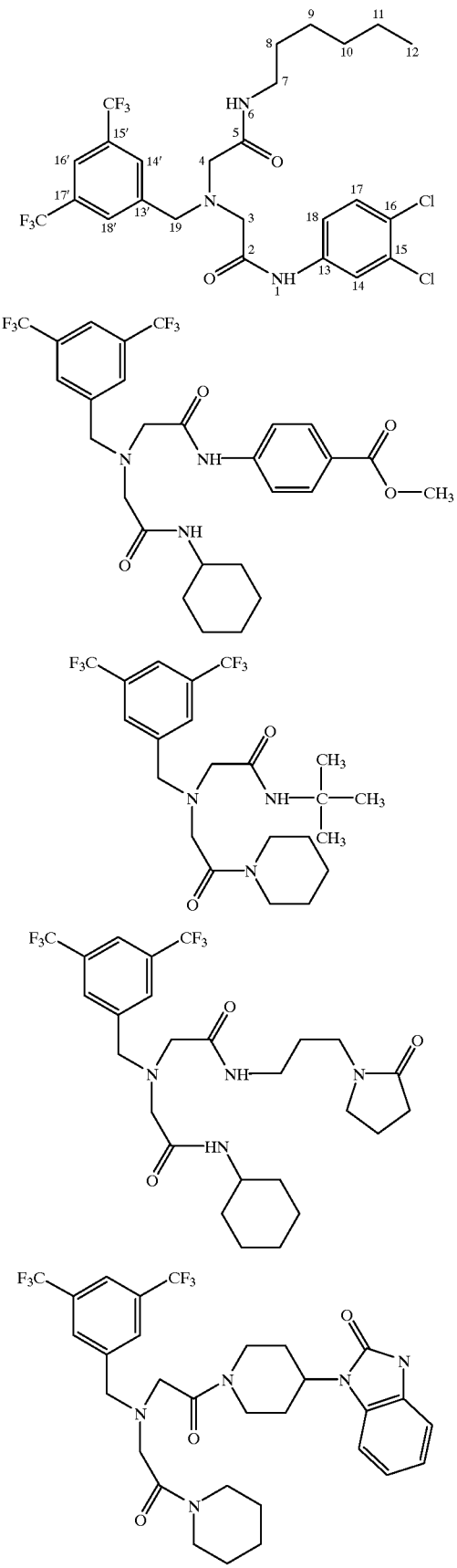

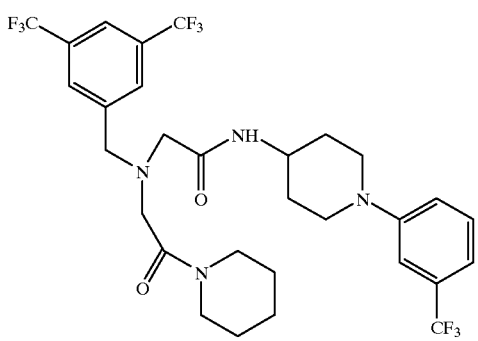
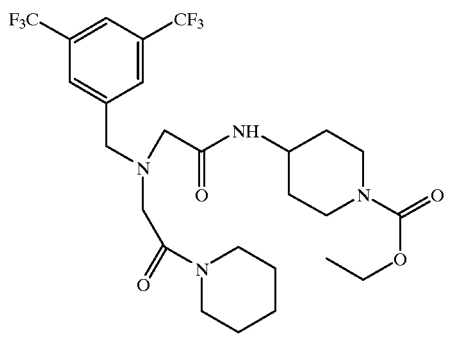
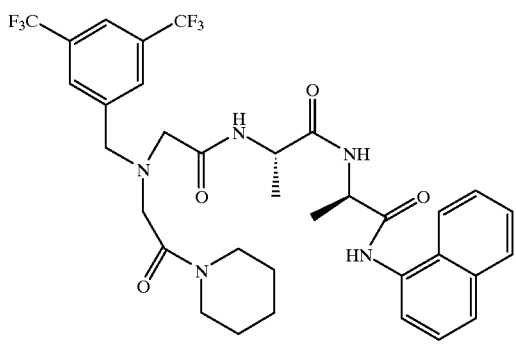
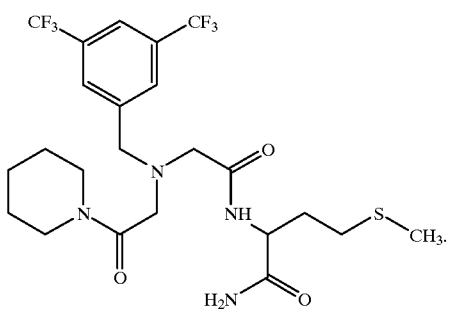

6. A composition comprising, in a physiologically acceptable medium, at least one compound corresponding to the following formula (I):

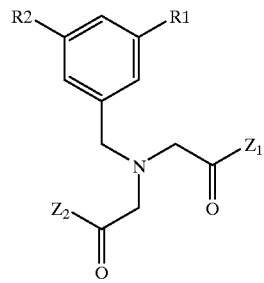

in which:

R₁ and R₂, which are identical or different, are chosen from hydrogen, a $CH_3$ radical, a $CF_3$ radical, a $OCH_3$ radical and an OH radical, $Z_1$ and $Z_2$ have the same meaning as in claim 1.

7. A composition according to claim 6, wherein the $R_1$ and $R_2$ radicals are each $CF_3$.

8. A composition according to claim 6, wherein the $Z_1$ and $Z_2$ radicals, which are the same or different, are chosen from piperidine and methionamide.

9. A composition according to claim 6, wherein:

the $R_1$ and $R_2$ radicals are each $CF_3$, and the $Z_1$ and $Z_2$ radicals, which are the same or different, are chosen from piperidine and methionamide.

10. A composition according to claim 6, comprising at least one compound of Formula (I) corresponding to one of the following formulae:

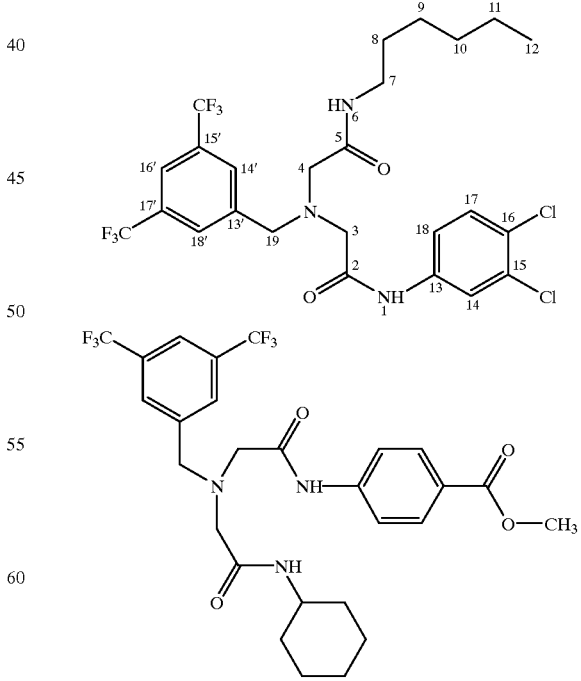

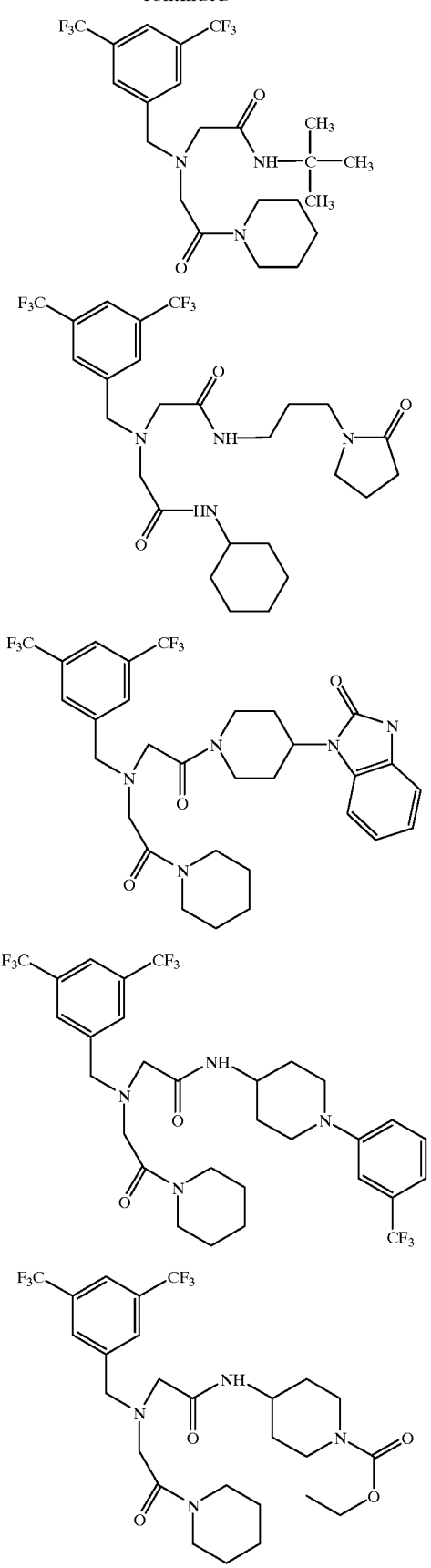

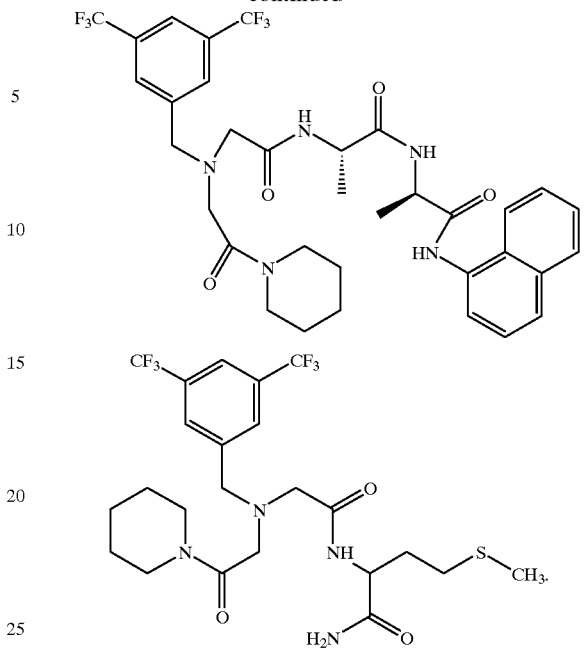

11. A composition according to claim 6, wherein the compound of formula (I) is present in an amount ranging from 0.001% to 20% by weight, relative to the total weight of the composition.

12. A composition according to claim 11, wherein the compound of formula (I) is present in an amount ranging from 0.01% to 10% by weight, relative to the total weight of the composition.

13. A composition according to claim 12, wherein the compound of formula (I) is present in an amount ranging from 0.01% to 5% by weight, relative to the total weight of the composition.

14. A composition according claim 6, wherein the composition is in a form chosen from an aqueous solution, an alcoholic solution, an aqueous/alcoholic solution, an oily solution, a dispersion, a water-in-oil emulsion, an oil-in-water emulsion, a suspension or emulsion with a soft consistency, microcapsules, microparticles, nonionic vesicular dispersions, ionic vesicular dispersions, a cream, a gel, a foam, and an aerosol composition.

15. A composition according to claim 6, further comprising at least one active agent.

16. A composition according to claim 15, wherein said active agent is chosen from agents which modulate cutaneous pigmentation, agents which modulate cutaneous proliferation, agents which modulate cutaneous differentiation, antibacterial agents, agents for combating parasites, antifungal agents, antiviral agents, steroidal anti-inflammatory agents, anaesthetic agents, antipruriginous agents, keratolytic agents, agents for combating free radicals, antiseborrhoeics, antidandruff agents, and antiacne agents.

17. A composition according to claim 6, further comprising at least one product having an irritant effect.

18. A composition according to claim 17, wherein the at least one product having an irritant effect is chosen from surfactants, preservatives, organic solvents, and active principles.

19. A composition according to claim 18, wherein the active principle is chosen from α-hydroxy acids, β-hydroxy acids, α-keto acids, β-keto acids, retinoids, anthralins, anthranoids, peroxides, minoxidil, lithium salts, antimetabolites, vitamin D and its derivatives, hair dyes, hair colorants, perfuming alcoholic solutions, antiperspirant agents, depilatory agents, permanent-wave agents, and depigmenting agents.

20. A composition according to claim 18, wherein the active principle is a hydrophilic active principle.

21. A composition according to claim 20, wherein the hydrophilic active principle is chosen from proteins, protein hydrosylates, amino acids, polyols, urea, allantoin, sugars, sugar derivatives, water-soluble vitamins, plant extracts, hydroxy acids, retinol (vitamin A) and its derivatives, tocopherol (vitamin E) and its derivatives, essential fatty acids, ceramides, essential oils, and salicylic acid and its derivatives.

22. A composition according to claim 6, further comprising at least one compound which decreases at least one of the synthesis, release, and activity of at least one mediator of inflammation.

23. A composition according to claim 6, wherein the composition is in a form chosen from a lotion, a gel, and a foam.

24. A composition according to claim 6, wherein the composition is in a form chosen from a cleansing cream, a protective cream, a treatment cream, a care cream, a liquid foundation, a make-up removal milk, a protective body milk, a care body milk, an anti-sun milk, an after-sun care cream, a cleansing lotion, an antisun lotion, an artificial tanning lotion, a bath or deodorizing composition comprising a bactericidal agent, an aftershave gel, an aftershave lotion, a depilatory cream, a composition for combating insect stings, a pain-control composition, a composition for treating certain cutaneous disorders, a solid composition in the form of a cleansing bar or soap, an aerosol composition, a hair-care composition, a shampoo, a hair-setting lotion, a hair-treating lotion, a styling gel, a styling cream, a dye composition, a coloring shampoo, a hair-structuring lotion, a permanent-wave composition, a lotion or gel for combating hair loss, a shampoo for combating parasites, and a composition for oral use.

25. A composition according to claim 6, wherein said composition is in a cosmetically acceptable medium.

26. Process for the preparation of a compound of formula (Ia) according to claim 1, comprising
   (A) reacting a diacid with a dehydrating agent to obtain an intermediate anhydride;
   (B) reacting the intermediate anhydride with one equivalent of a first amine or alcohol; and
   (C) reacting the intermediate anhydride with one equivalent of a second amine or alcohol.

27. A process for weakening or eliminating the irritant effect of a product having an irritant effect, said process comprising combining with said product an effective amount of at least one compound of formula (Ia) according to claim 1.

28. A process for weakening or eliminating the irritant effect of a product having an irritant effect, said process comprising combining with said product an effective amount of a composition according to claim 6.

29. A process for treating or preventing a cutaneous disorder, said process comprising applying an effective amount of a compound of formula (Ia) according to claim 1 in the form of a physiologically acceptable composition to a locus in need thereof.

30. A process for treating or preventing a cutaneous disorder, said process comprising applying to a locus in need thereof an effective amount of a composition according to claim 6.

31. A process according to claim 29, wherein said cutaneous disorder is chosen from cutaneous irritations, sores, redness, dysaesthetic sensations, warming sensations, pruritus of the skin, and pruritus of the mucous membranes.

32. A process according to claim 30, wherein said cutaneous disorder is chosen from cutaneous irritations, sores, redness, dysaesthetic sensations, warming sensations, pruritus of the skin, and pruritus of the mucous membranes.

33. A process for treating sensitive skin comprising applying to the skin an effective amount of a compound of formula (Ia) according to claim 1 in the form of a physiologically acceptable composition.

34. A process for treating sensitive skin comprising applying to the skin an effective amount of a composition according to claim 6.

35. A process for cosmetically treating membranes, said process comprising applying to the skin, the hair, or the mucous an effective amount of a composition according to claim 6.

* * * * *

UNITED STATES PATENT AND TRADEMARK OFFICE
CERTIFICATE OF CORRECTION

PATENT NO. : 6,291,478 B1
DATED : September 18, 2001
INVENTOR(S) : Jean-Baptiste Galey et al.

It is certified that error appears in the above-identified patent and that said Letters Patent is hereby corrected as shown below:

Column 24,
Line 37, "from 0.01%" should read -- from 0.1% --.
Line 39, "according claim 6" should read -- according to claim 6 --.

Signed and Sealed this

Fourteenth Day of May, 2002

Attest:

JAMES E. ROGAN
Attesting Officer     Director of the United States Patent and Trademark Office